T860,014

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED MARCH 25, 1969

860 O.G. 1007

764,023

SYNTHESIS OF ACRYLONITRILE FROM PROPYLENE, AMMONIA AND OXYGEN

Edgar L. McDaniel and Howard S. Young, both % Tennessee Eastman Company, P.O. Box 511, Kingsport, Tenn. 37662

Continuation of application Ser. No. 523,267, Jan. 27, 1966. This application Sept. 19, 1968. Published Mar. 25, 1969

Class 252—437

No Drawing. 13 Pages Specification

Acrylonitrile is prepared by reacting propylene, ammonia and oxygen in the vapor phase in the presence of a novel catalyst comprising an oxide of arsenic and an inorganic heteropoly acid containing phosphorus and vanadium and optionally tungsten, such as phospho-12-vanadic acid or phospho-12-vanadotungstic acid. The arsenic, phosphorus, vanadium and optionally tungsten all are in an oxidized form, the degree of oxidation of any or all of these components being variable within certain ranges as indicated by the following empirical formula:

$$As_aP_bV_cW_dO_exH_2O$$

wherein:

$a$=0.1–30
$b$=1–4
$c$=2–12, and
$d$=0–10, and wherein the sum of $c$ and $d$ does not exceed 12, and $e=\frac{1}{2}(a.m+b.n+c.p+d.q)$ and wherein:

$m$=average valence of As in catalyst $n$=average valence of P in catalyst $p$=average valence of V in catalyst $q$=average valence of W in catalyst, and X=0–10.

Preferred catalyst compositions have the following characteristics:

$$a=0.5–10$$

and $$b=1–2$$

with $c$, $d$, $e$ and $x$ remaining as above.

The catalyst can be supported on suitable carriers, such as silica gel, kieselguhr, silicon carbide, etc.

Acrylonitrile is prepared by reacting propylene ammonia and oxygen at temperatures of 350–600° C., the preferred range being 425–575° C. While reactant ratios near stoichiometric values are preferred, the ratios can vary from propylene:oxygen ratios of 1:0.2–5 and propylene:ammonia ratios of 1:0.2–3.